(12) United States Patent
Chen et al.

(10) Patent No.: US 8,691,870 B2
(45) Date of Patent: Apr. 8, 2014

(54) USE OF ISOTHIOCYANATES FOR TREATING CANCER

(75) Inventors: Yu-Jen Chen, Taipei (TW); Hui-Fen Liao, Chiayi (TW)

(73) Assignee: Mackay Memorial Hospital, Taipei (TW)

( * ) Notice: Subject to any disclaimer, the term of this patent is extended or adjusted under 35 U.S.C. 154(b) by 95 days.

(21) Appl. No.: 13/243,128

(22) Filed: Sep. 23, 2011

(65) Prior Publication Data

US 2013/0079401 A1   Mar. 28, 2013

(51) Int. Cl.
*A61K 31/26* (2006.01)
*C07C 331/00* (2006.01)

(52) U.S. Cl.
USPC ............................................ 514/514; 558/17

(58) Field of Classification Search
USPC ............................................ 514/514; 558/17
See application file for complete search history.

(56) References Cited

U.S. PATENT DOCUMENTS

2006/0020046 A1*  1/2006  Goralczyk et al. ............. 514/763
2008/0095869 A1*  4/2008  Archibald et al. ............. 424/760

OTHER PUBLICATIONS

Naturopathic Doctor News and Review (NDNR) (Aug. 2007, 7 pages).*
Wantanabe (Phytochemistry 62(2003)733-739).*
Bauer (Clinical Journal of Oncology Nursing, vol. 13, No. 5, 523-534).*
Volpe et al. (cancer Letters 274 (2009) 1-9).*
Zhang et al. (Leukemia (2008) 22(6).*
Sheridan (J. Chem. Inf. Comput. Sci. 2002, 42, 103-108).*

* cited by examiner

*Primary Examiner* — Shirley V Gembeh
(74) *Attorney, Agent, or Firm* — Muncy, Geissler, Olds & Lowe, P.C.

(57) ABSTRACT

Novel Uses of small molecules, particularly, 6-methylsulfinylhexyl isothiocyanate and 6-methylsulfonylhexyl isothiocyanate, are disclosed herein. The two isothiocyanates are useful as lead compounds for manufacturing a medicament or a pharmaceutical composition for treating cancer, particularly drug-resistant cancer, in a patient.

2 Claims, 10 Drawing Sheets
(2 of 10 Drawing Sheet(s) Filed in Color)

USE OF ISOTHIOCYANATES FOR TREATING CANCER

BACKGROUND OF THE INVENTION

1. Field of the Invention

The present disclosure relates to novel use of small molecules, particularly, use of isothiocyanates as lead compounds for manufacturing a medicament or a pharmaceutical composition for treating cancer.

2. Description of Related Art

Cancer has become the major cause of death in most countries. Currently, there are four standard methods of treatment for cancer: surgery, chemotherapy, radiation therapy, immunotherapy, and biologic therapy; among them, surgery and chemotherapy remain the most adopted means for cancer treatment.

Complete removal of the cancer without damage to the rest of the body is the goal of the treatment, sometimes this can be achieved by surgery, but the propensity of cancers to invade adjacent tissue or to spread to distant sites by microscopic metastasis often limits its effectiveness. Chemotherapy is the treatment of cancer with drugs that can destroy cancer cells. In current usage, the term "chemotherapy" usually refers to cytotoxic drugs which affect rapidly dividing cells in general. However, in some occasions, cancerous cells develop resistance or are insensitive toward one or more cytotoxic drugs, thereby rendering these drug(s) useless for the treatment of cancer. Hence, many attempts have been made to locate other effective drugs or means for successful treatment of cancer, especially drug resistant- or chemotherapeutic agent insensitive-cancer. Further, some cancers have poor prognosis or are insensitive to current chemotherapeutic agents, such as pancreatic cancer, non-small-cell lung cancer or esophageal cancer.

Therefore, there is a need in the related art an agent or a compound that may be useful for the treatment of above-described cancers, including drug-resistance cancers or cancers that are insensitive to current chemotherapeutic agents.

SUMMARY

The present disclosure is based, at least in part, unexpected discovery that an isothiocyanate isolated from Wasabi (*Wasabia japonica* MATSUM), 6-methylsulfinylhexyl isothiocyanate (hereafter I7457); and its derivative, 6-methylsulfonyl-hexyl isothiocyanate (hereafter I7557), respectively may retard the growth of cancerous cells by arresting at least 45% of the cancerous cells at $G_2/M$ phase. The results of this invention suggest that these two compounds are potential lead compounds for use as therapeutic agents for treating cancers, including cancers that are drug-resistant.

Accordingly, it is the first aspect of this disclosure to provide a method of treating cancer in a subject. The method comprises administering to the subject a therapeutically effective amount of I7457 or I7557 or a pharmaceutically acceptable salt thereof. The cancer suitable for treating by the method of this disclosure is selected from the group consisting of pancreatic cancer, chronic myelogenous leukemia (CML), non-small-cell lung carcinoma, and esophageal cancer. In one preferred example, the CML is resistant to imatinib. The subject may be a mammal, preferably a human.

In some embodiments, the method further comprises subjecting the cancer to radiation treatment after administering the compounds of this invention to the subject. In one example, the cancer is pancreatic cancer.

In further embodiments, the method further comprises administering to the subject another agent that is known to improve the treatment of cancer before, together with and/or after administering I7457 or I7557. Examples of such agent include, but are not limited to, anti-cancer drug, angiogenesis inhibitor, anti-virus agent, antibiotic, analgesic, anti-anemia drug, cytokine, granulocyte colony-stimulating factor (G-CSF), anti-nausea drug, and the like.

It is therefore the second aspect of this disclosure to provide a use of I7457 or I7557 for manufacturing a medicament or a pharmaceutical composition for treating cancer; the medicament or the pharmaceutical composition comprises a therapeutically effective amount of I7457 or I7557 or a pharmaceutically acceptable salt thereof; and a pharmaceutically acceptable excipient.

The compound of this invention, specifically I7457 or I7557, is present at a level of about 0.1% to 99% by weight, based on the total weight of the pharmaceutical composition. In some embodiments, the compound of this invention is present at a level of at least 1% by weight, based on the total weight of the pharmaceutical composition. In certain embodiments, the compound of this invention is present at a level of at least 5% by weight, based on the total weight of the pharmaceutical composition. In still other embodiments, the compound of this invention is present at a level of at least 10% by weight, based on the total weight of the pharmaceutical composition. In still yet other embodiments, the compound of this invention is present at a level of at least 25% by weight, based on the total weight of the pharmaceutical composition.

In some embodiments, the medicament or the pharmaceutical composition of this invention further includes an agent that is known to improve the treatment of cancer. Examples of such agent include, but are not limited to, anti-cancer drug, angiogenesis inhibitor, anti-virus agent, antibiotic, analgesic, anti-anemia drug, cytokine, granulocyte colony-stimulating factor (G-CSF), anti-nausea drug, and the like.

The details of one or more embodiments of the invention are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The patent or application file contains at least one drawing executed in color. Copies of this patent or patent application publication with color drawing(s) will be provided by the Office upon request and payment of the necessary fee.

Figure 1:
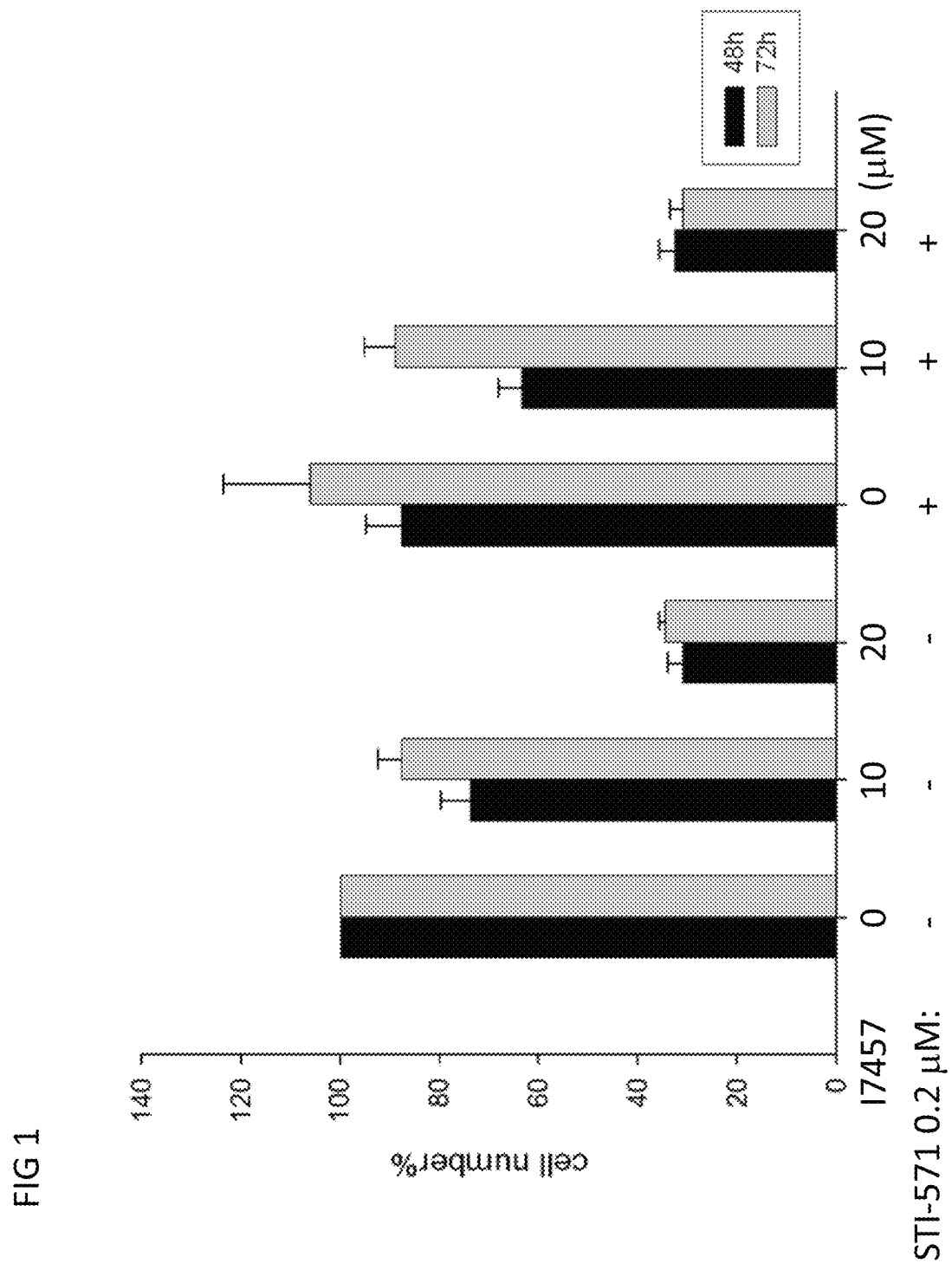
Figure 2:
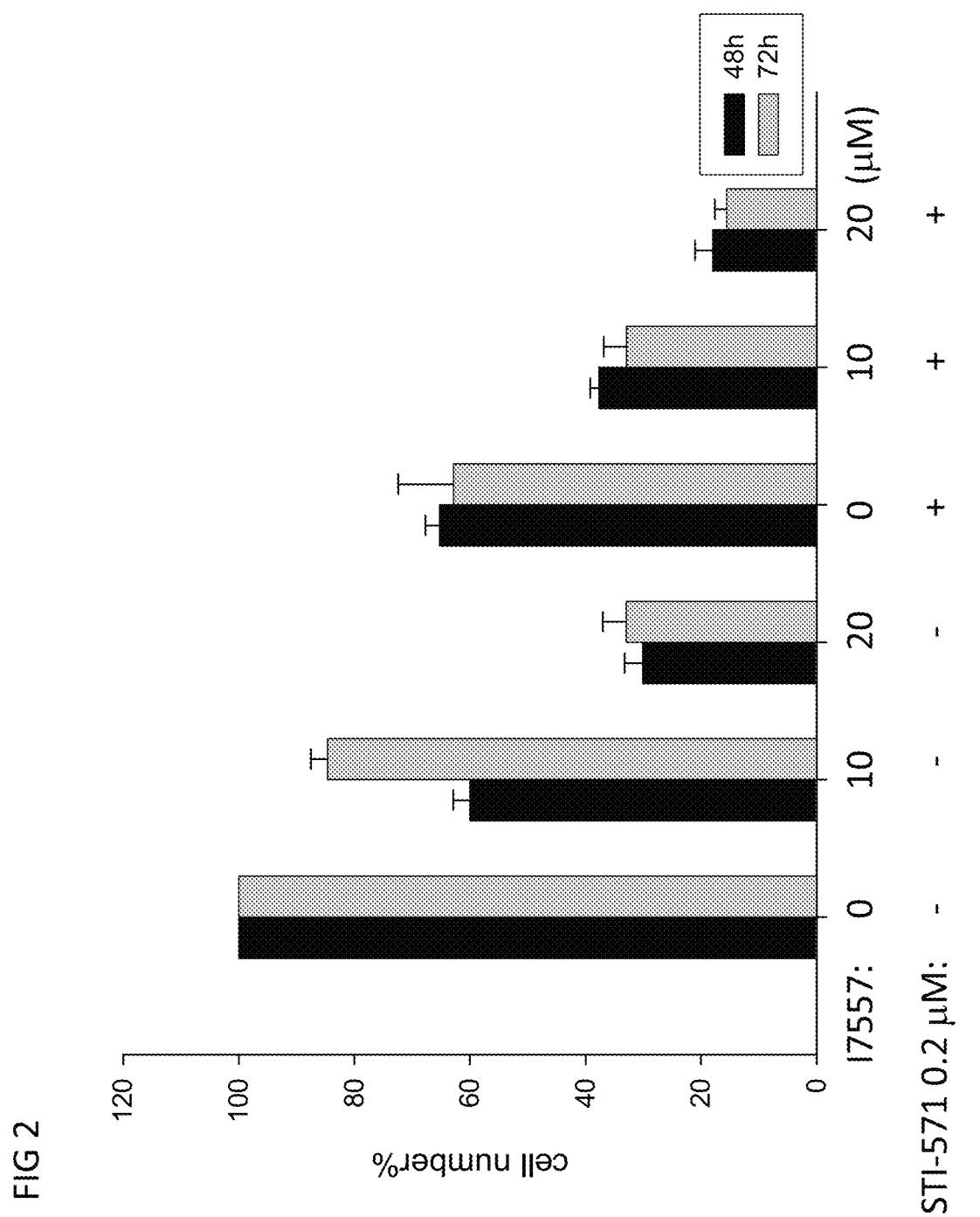
Figure 3:
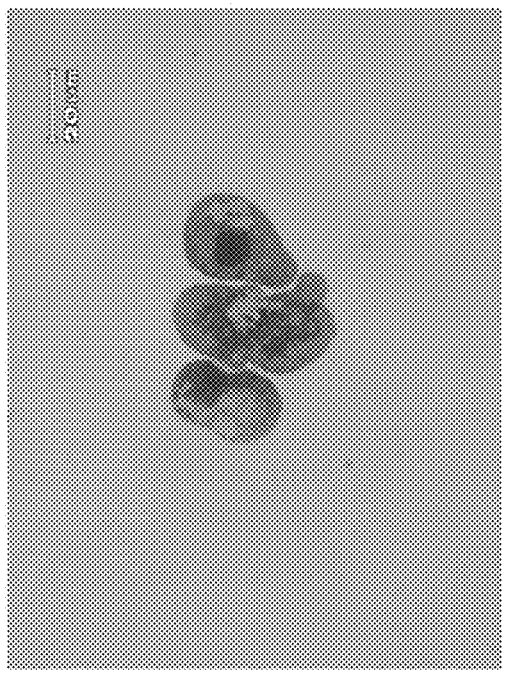
Figure 3:
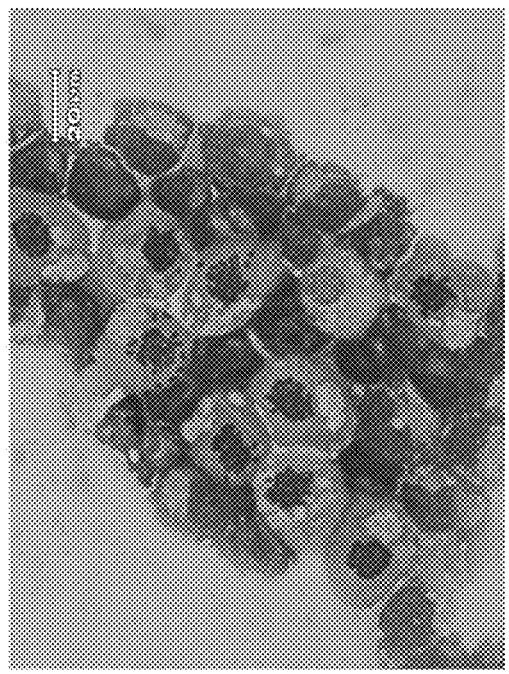
Figure 3:
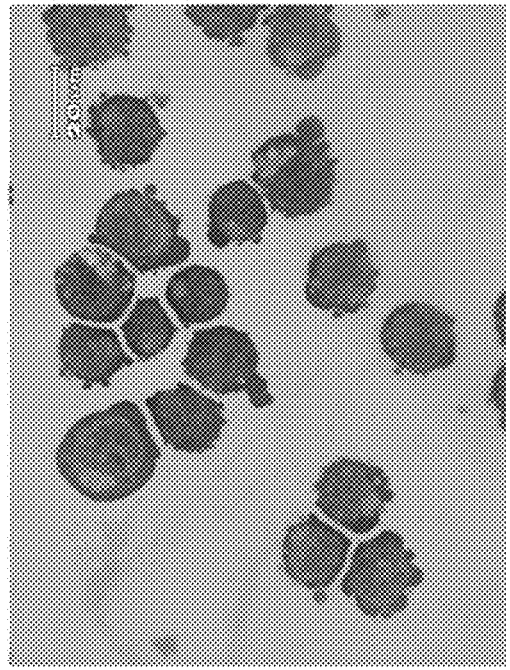
Figure 4:
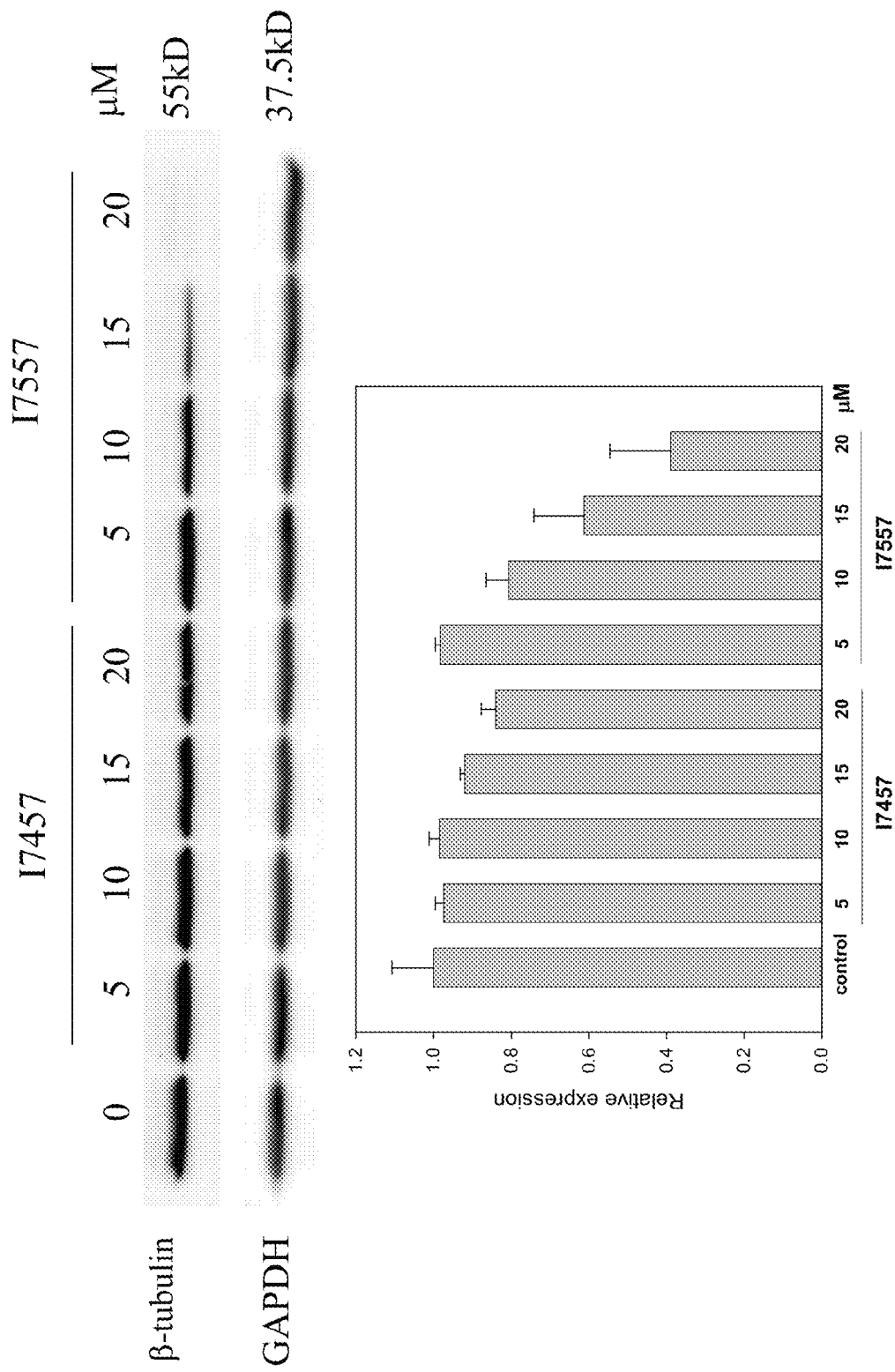
Figure 5:
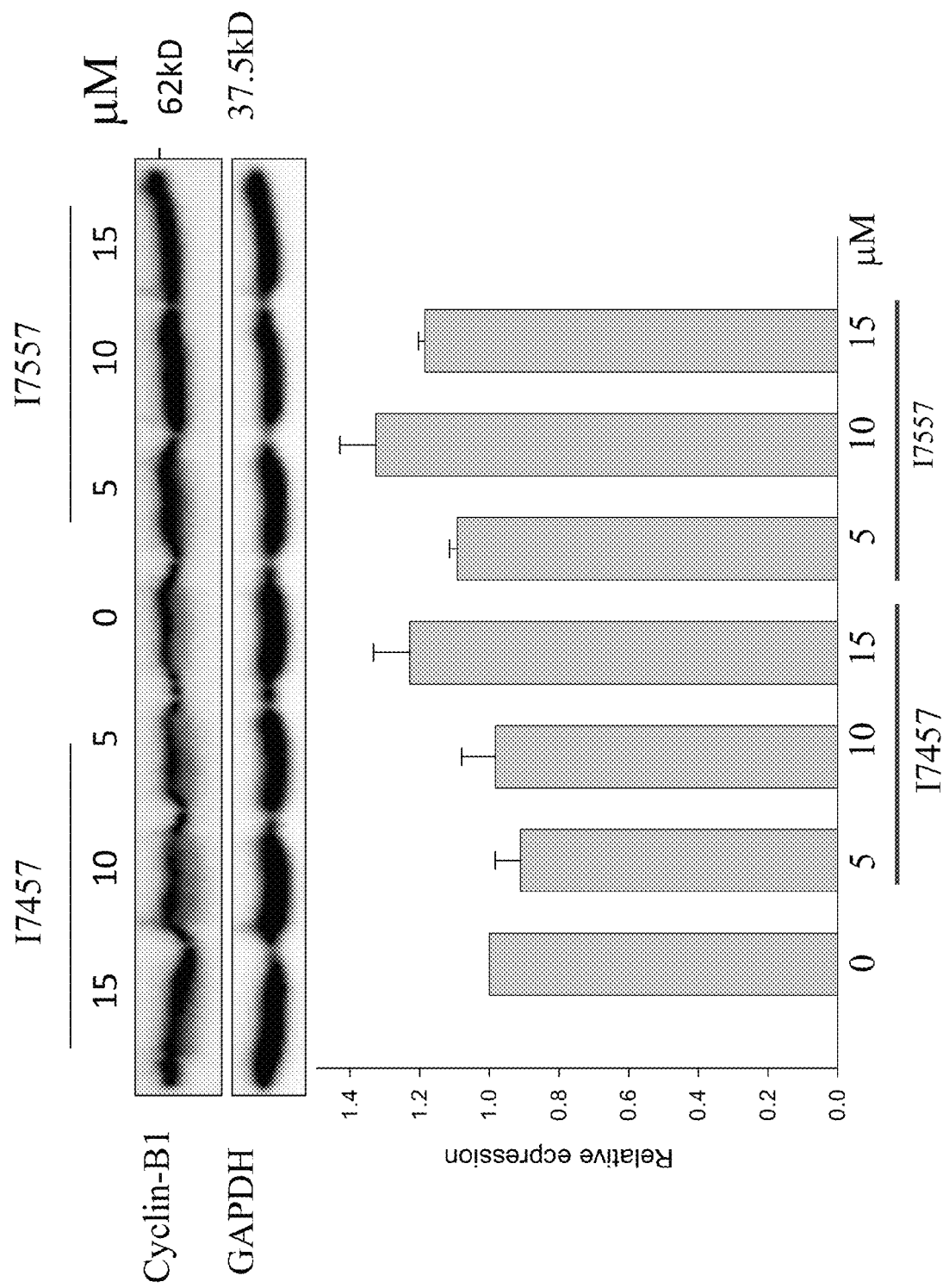
Figure 6:
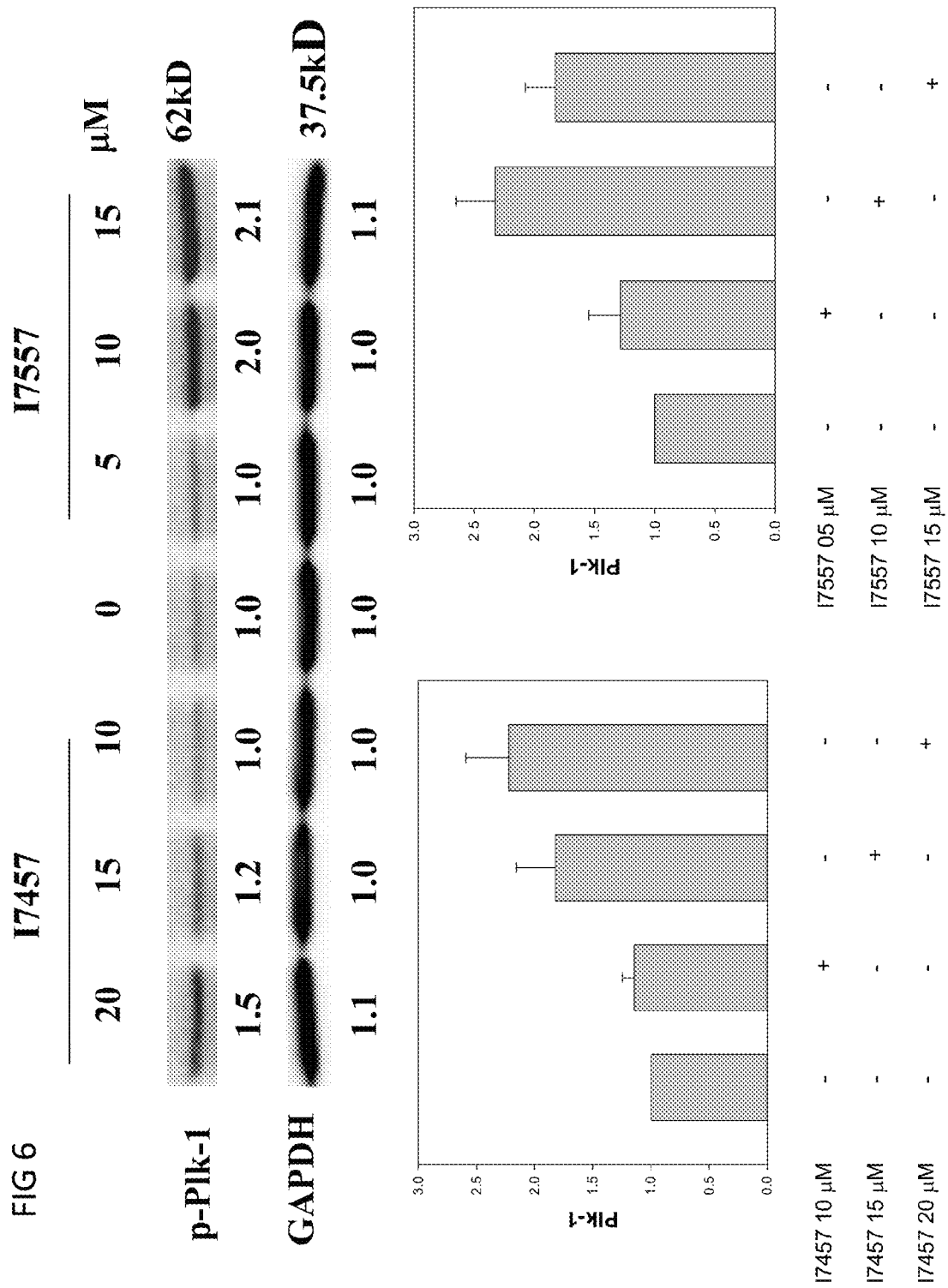
Figure 7:
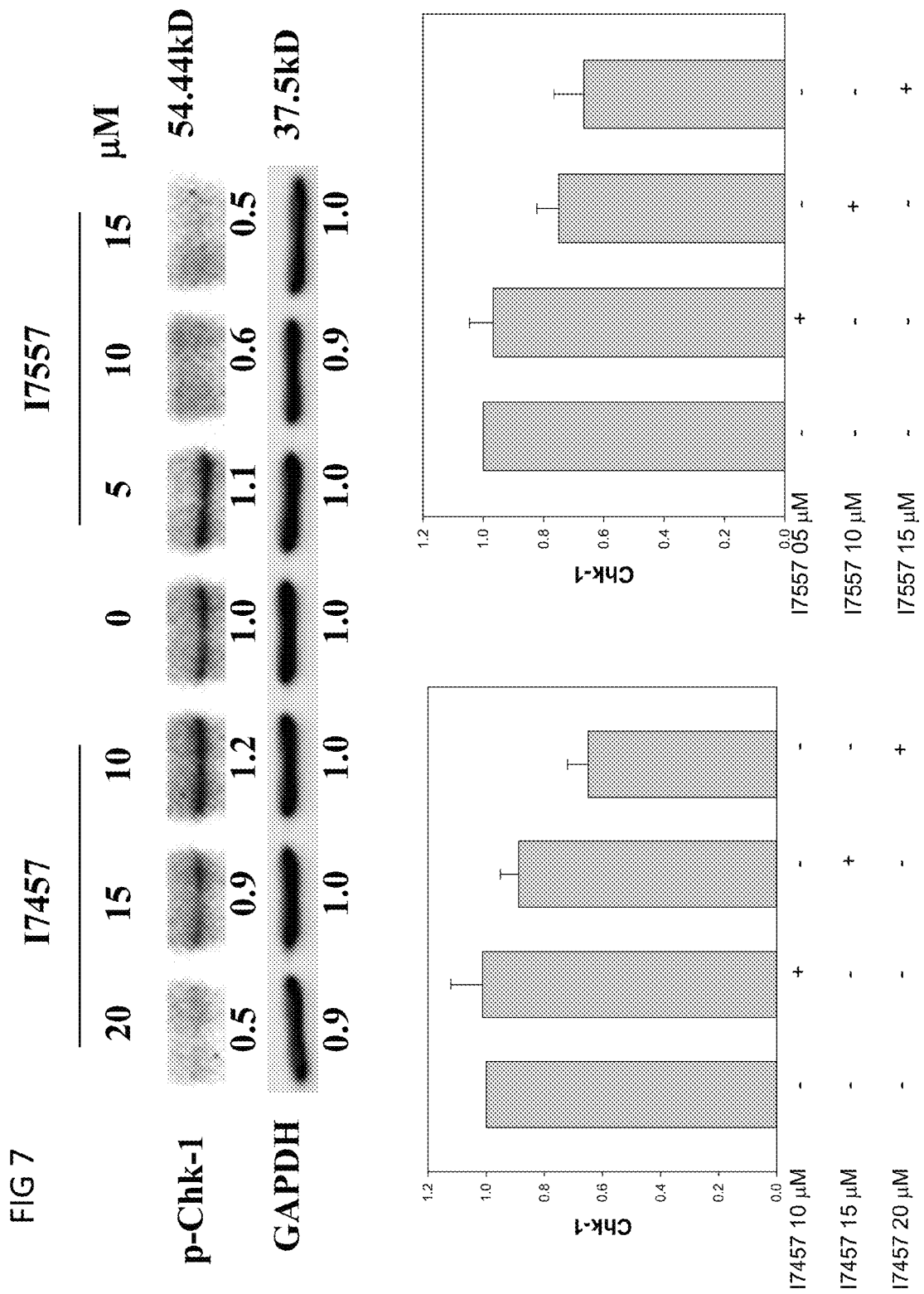
Figure 8:
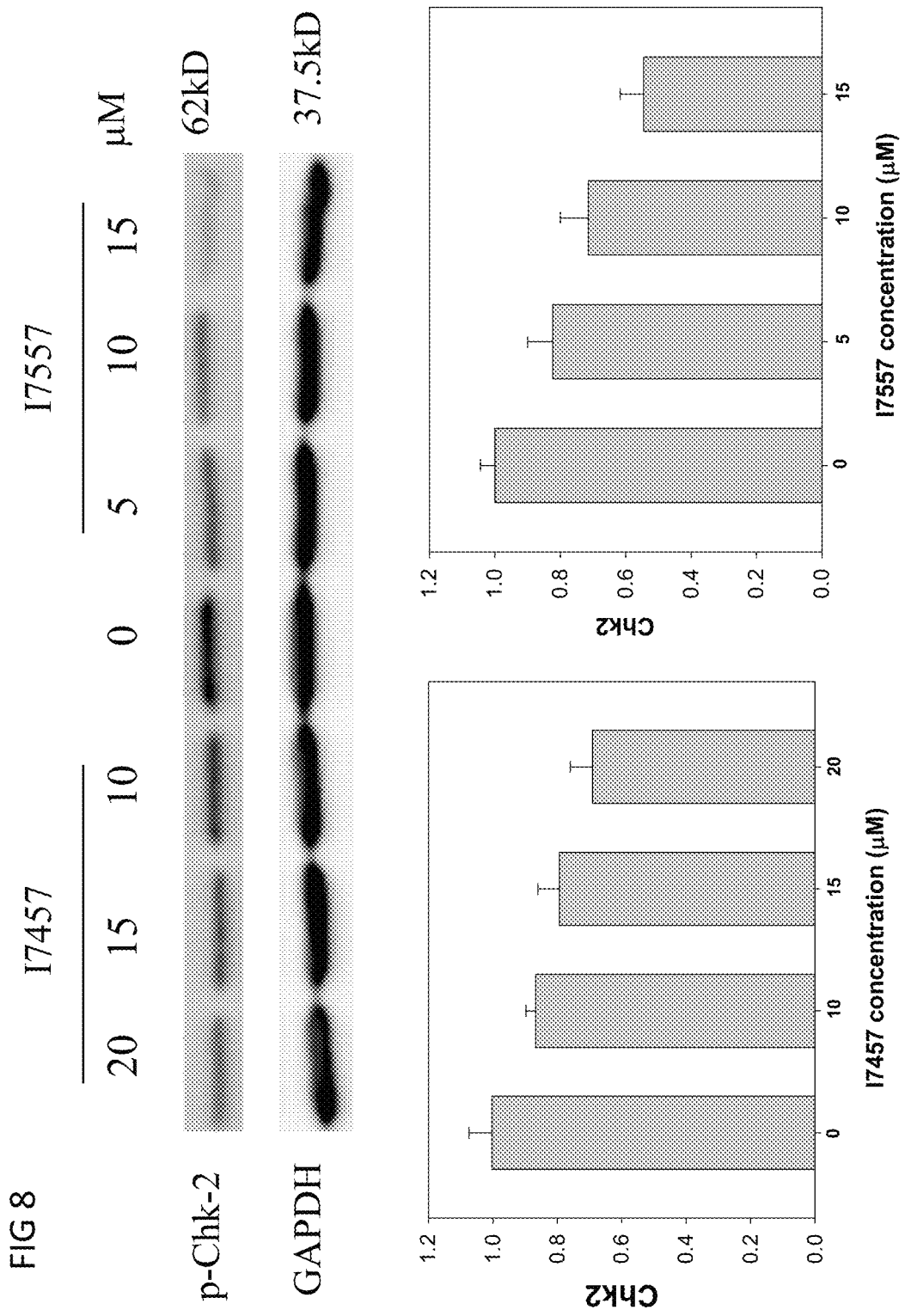
Figure 9:
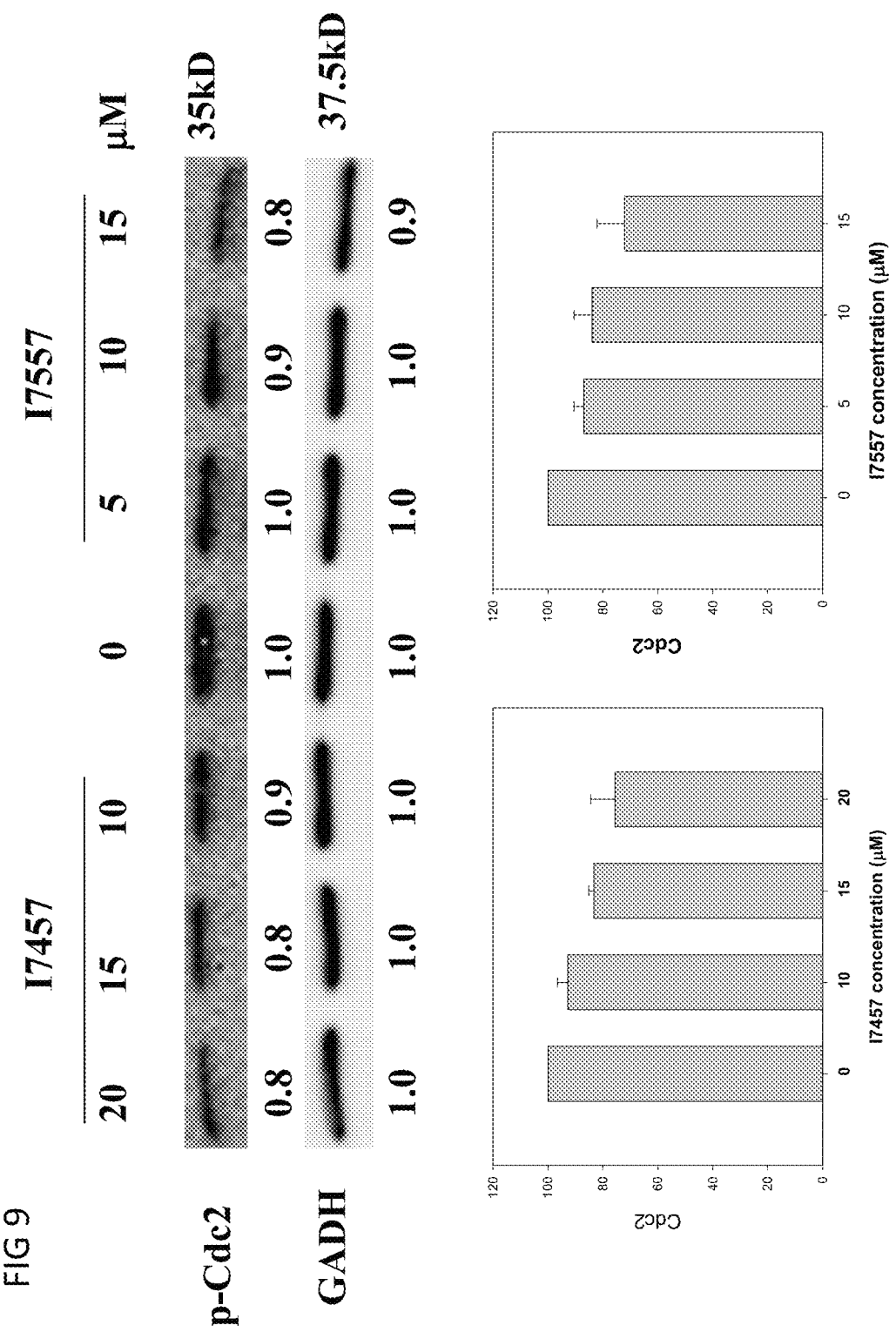
Figure 10:
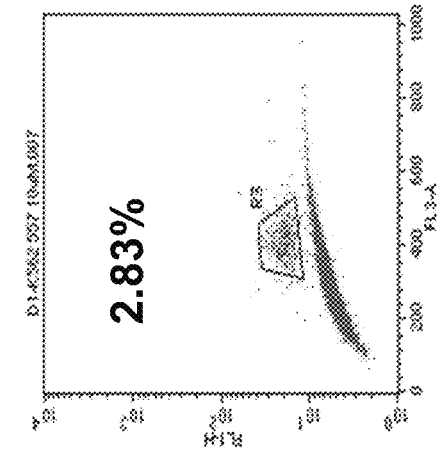
Figure 10:
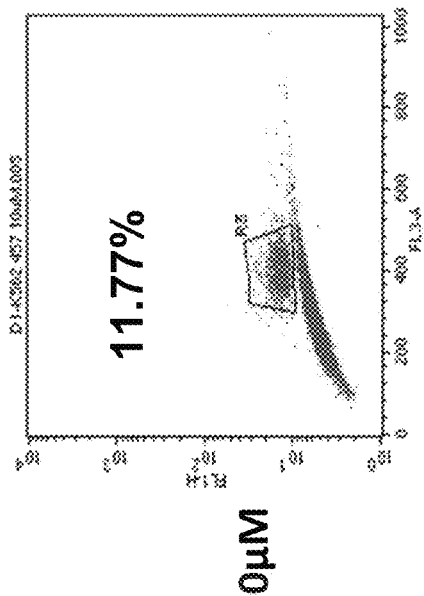
Figure 10:
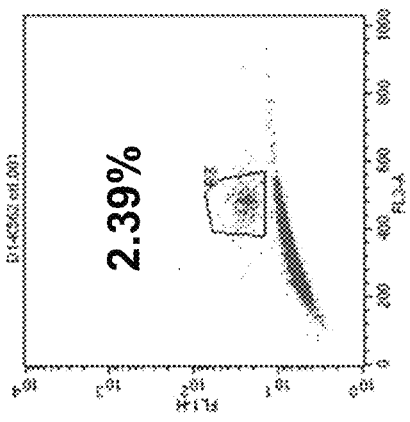
Figure 10:
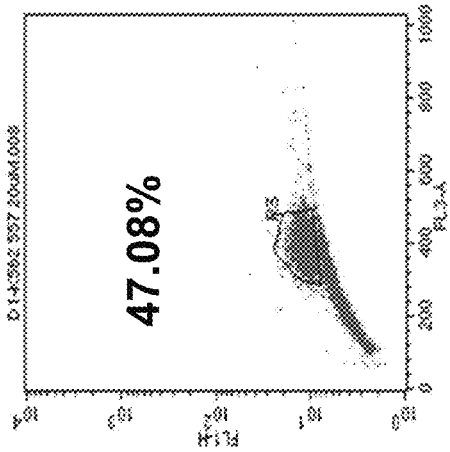
Figure 10:
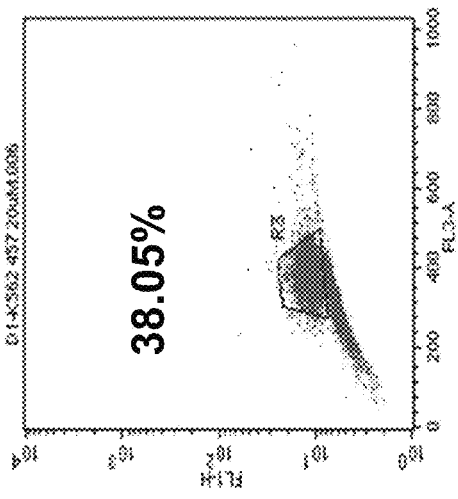
Figure 10:
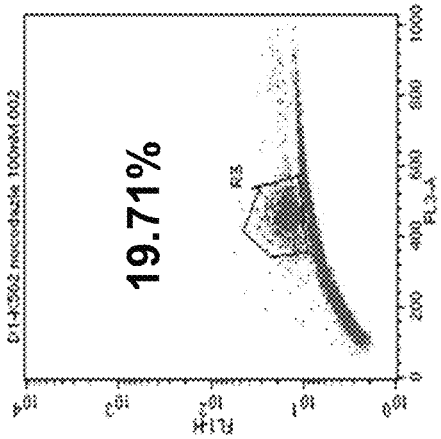

The present description will be better understood from the following detailed description read in light of the accompanying drawings, wherein:

FIG. 1 illustrates the effects of I7457 on cell viability of imatinib resistant CML K562R cells in accordance with one embodiment of this invention;

FIG. 2 illustrates the effects of I7557 on cell viability of imatinib resistant CML K562R cells in accordance with one embodiment of this invention;

FIG. 3 are photographs of imatinib resistant CML K562R cells after being stained by Liu's staining in accordance with one embodiment of this invention, in which (A) is the control cells, (B) is 20 μM I7457-treated cells, and (C) is 20 μM I7557-treated cells;

FIG. 4 illustrates the levels of β-tubulin in I7457- and I7557-treated imatinib resistant CML K562R cells respectively in accordance with one embodiment of this invention;

FIG. 5 illustrates the levels of cyclin-B1 in I7457- and I7557-treated imatinib resistant CML K562R cells respectively in accordance with one embodiment of this invention;

FIG. 6 illustrates the levels of p-Plk-1 in I7457- and I7557-treated imatinib resistant CML K562R cells respectively in accordance with one embodiment of this invention;

FIG. 7 illustrates the levels of p-Chk-1 in I7457- and I7557-treated imatinib resistant CML K562R cells respectively in accordance with one embodiment of this invention;

FIG. 8 illustrates the levels of p-Chk-2 in I7457- and I7557-treated imatinib resistant CML K562R cells respectively in accordance with one embodiment of this invention;

FIG. 9 illustrates the levels of p-Cdc2 kinase in I7457- and I7557-treated imatinib resistant CML K562R cells respectively in accordance with one embodiment of this invention; and FIG. 10 illustrates the expressed level of phosphorylated histone H3 in I7457- and I7557-treated imatinib resistant CML K562R cells respectively in accordance with one embodiment of this invention.

DETAILED DESCRIPTION OF PREFERRED EMBODIMENTS

The detailed description provided below in connection with the appended drawings is intended as a description of the present invention and is not intended to represent the only forms in which the present invention may be constructed or utilized.

The present disclosure is based, at least in part, unexpected discovery that two isothiocyanates possess anti-proliferative activity toward cancerous cells, including drug-resistant cancerous cells. One compound, 6-methylsulfinylhexyl isothiocyanate or I7457, is isolated from Wasabi (*Wasabia japonica* MATSUM); the other compound, 6-methylsulfonylhexyl isothiocyanate or I7557, is derived from I7457. Therefore, these active isothiocyanates are potential lead compounds for use as therapeutic agents for treating cancer.

Isothiocyanates are compounds containing the isothiocyanate (—NCS—) moiety and are readily identifiable. Shown below are chemical structures of the two active isothiocyanates of this disclosure.

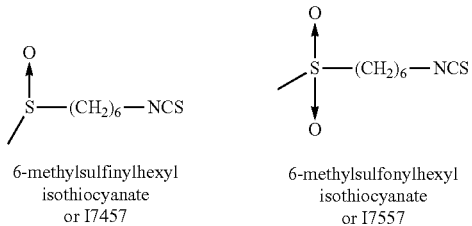

6-methylsulfinylhexyl isothiocyanate or I7457

6-methylsulfonylhexyl isothiocyanate or I7557

6-methylsulfinylhexyl isothiocyanate (or I7457) of this invention can be purified from plants, seeds, or plant extracts by methods well known in the art. Plants having high levels of isothiocyanates include, but are not limited to, broccoli, sprouts, cabbage, cauliflower, mustard seed, wasabi, radish, and papaya seeds. Preferably, I7457 was isolated from wasabi (*Wasabi japonica* MATSUM). 6-methylsulfonylhexyl isothiocyanate (or I7557), on the other hand, is a derivative of I7457, and can be purchased from laboratories such as LKT Laboratories, Inc (St. Paul, Minn., USA).

Accordingly, this disclosure provides a method of treating cancer in a subject. The method includes administering to the subject an effective amount of any of the two compounds described above or a pharmaceutically acceptable salt thereof. The two compounds of this disclosure are effective in treating cancer by arresting at least 45% of the cancerous cells at $G_2/M$ cycle, preventing them from multiplying. Cancer that may be treated by the compounds of this disclosure includes pancreatic cancer, chronic myelogenous leukemia (CML), non-small-cell lung carcinoma (NSCLC), and esophageal cancer. Preferably, the compounds of this disclosure are employed to treat drug-resistant cancers.

As used herein, drug-resistance refers to a state of cancer in which, having developed resistance to a single drug. For example, a cancer that has developed drug-resistance can show resistance to vinca alkaloids (e.g., vinblastine, vincristine, and vinorelvine); anthracyclines (e.g., doxorubicin, daunorubicin, and idarubicin); microtubule-stabilizing drug paclitaxel; or drugs that target tyrosine kinases (TKs) activity (e.g., dasatinib, nilotinib, and imatinib).

In one preferred example, the cancer that may be treated by any of the two compounds of this disclosure is CML, particularly, CML that has developed drug-resistance to the FDA approved drug, imatinib. In another example, the cancer that may be treated by any of the two compounds of this disclosure is pancreatic cancer, which has a poor prognosis and the median survival for locally advanced and for metastatic disease, is about 10 and 6 months respectively. In still another example, the cancer is NSCLC, which is insensitive to chemotherapy. In other example, the cancer is esophageal cancer, which surgery removal of the esophageal cancerous tissue remains the primary means for its treatment.

In some embodiments, the effective amount of the compounds of this invention administered to the subject is from about 1 to 100 mg/Kg body weight of the subject by oral ingestion, intravenous or intramuscular injection. The amount is administered to the subject at about 10, 20, 30, 40, 50, 60, 70, 80, 90 or 100 mg/Kg body weight of the subject per day, preferably about 30 to 70 mg/Kg body weight of the subject, such as 30, 40, 50, 60 or 70 mg/Kg body weight of the subject per day. The dose can be administered in a single dosage, or alternatively in more than one dosage.

In some embodiments, the method further includes the step of subjecting the cancer to a radiation treatment after administering the compounds of the invention. In one preferred example, the cancer is pancreatic cancer.

In some embodiments, the method further includes the step of administering another agent that is known to improve the treatment of cancer, before, together with and/or after administering the compound of this invention. Examples of such agent include, but are not limited to, anti-cancer drug, anti-angiogenesis agent, anti-virus agent, antibiotic, analgesic, anti-anemia drug, cytokine, granulocyte colony-stimulating factor (G-CSF), and anti-nausea drug and the like.

Examples of anti-cancer drug include, but are not limited to, paclitaxel, docetaxel, camptothecin (CPT), topotecan (TPT), irinotecan (CPT-11), Doxorubicin, daunorubicin, epirubicin, fluorouracil, cis-platin, cyclophosphamide, vinblastine, vincristine, ifosfamide, melphalan, mitomycin, methotrexate, mitoxantrone, teniposide, etoposide, bleomycin, leucovorin, cytarabine, dactinomycin, streptozocin, combretastatin A4-phosphate, SU5416, and the like. Examples of anti-angiogenesis agent include, but are not limited to, DS 4152, TNP-470, SU6668, endostatin, 2-methoxyestradiol, angiostatin, thalidomide, tetrathiomolybdate, linomide, IL-12, and the like. Examples of anti-virus agent include, but are not limited to, amantadine, rimantadine, and the like. Examples of analgesic include, but are not limited to, paracetamol such as para-acetylaminophenol, non-steroidal anti-inflammatory drug (NSAID) such as salicylates, and opioid drugs such as morphine and opium. Example of anti-anemia drug includes, and is not limited to, erythropoietin.

This disclosure also provides a pharmaceutical composition for treating cancer; the composition comprises a therapeutically effective amount of a compound of this disclosure as shown above; and a pharmaceutically acceptable excipient.

Generally, the compound of this invention is present at a level of about 0.1% to 99% by weight, based on the total weight of the pharmaceutical composition. In some embodiments, the compound of this invention is present at a level of at least 1% by weight, based on the total weight of the pharmaceutical composition. In certain embodiments, the compound of this invention is present at a level of at least 5% by weight, based on the total weight of the pharmaceutical composition. In still other embodiments, the compound of this invention is present at a level of at least 10% by weight, based on the total weight of the pharmaceutical composition. In still yet other embodiments, the compound of this invention is present at a level of at least 25% by weight, based on the total weight of the pharmaceutical composition.

In some embodiments, the medicament of said pharmaceutical composition of this invention further includes an agent that is known to improve the treatment of cancer. Examples of such agent include, and are not limited to, anti-cancer drug, anti-angiogenesis agent, anti-virus agent, antibiotic, analgesic, anti-anemia drug, cytokine, granulocyte colony-stimulating factor, anti-nausea drug and the like.

The medicament or said pharmaceutical composition is prepared in accordance with acceptable pharmaceutical procedures, such as described in Remington's Pharmaceutical Sciences, 17$^{th}$ edition, ed. Alfonoso R. Gennaro, Mack Publishing Company, Easton, Pa. (1985). Pharmaceutically acceptable excipients are those that are compatible with other ingredients in the formulation and biologically acceptable.

The compounds of this invention (e.g., I7457 or I7557) may be administered by any suitable route, for example, orally in capsules, suspensions or tablets or by parenterally administration. Parenterally administration can include, for example, systemic administration such as intramuscular, intravenous, subcutaneous, or intraperitoneal injection. The compound can also be administered transdermally either topically or by inhalation (e.g., intrabronichial, intranasal, oral inhalation or intranasal drops), or rectally, alone or in combination with conventional pharmaceutically acceptable excipients. In preferred embodiments, the compounds of this invention are administered orally (e.g., dietary) to the subject.

For oral administration, the compounds of the present invention may be formulated into tablets containing various excipients such as microcrystalline cellulose, sodium citrate, calcium carbonate, dicalcium phosphate, and glycine; along with various disintegrants such as starch, alginic acid and certain silicates; together with granulation binders like polyvinylpyrrolidone, sucrose, gelatin and acacia. Additionally, lubricating agents such as magnesium stearate, sodium lauryl sulfate and talc may be added. Solid composition may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and if so desired, emulsifying and/or suspending agents as well, together with diluents such as water, ethanol, propylene glycol, glycerin and a combination thereof.

For parenteral administration, the compounds of the present invention may be formulated into liquid pharmaceutical compositions, which are sterile solutions, or suspensions that can be administered by, for example, intravenous, intramuscular, subcutaneous, or intraperitoneal injection. Suitable diluents or solvent for manufacturing sterile injectable solution or suspension include, but are not limited to, 1,3-butanediol, mannitol, water, Ringer's solution, and isotonic sodium chloride solution. Fatty acids, such as oleic acid and its glyceride derivatives are also useful for preparing injectables, as are natural pharmaceutically-acceptable oils, such as olive oil or castor oil. These oil solutions or suspensions may also contain alcohol diluent or carboxymethyl cellulose or similar dispersing agents. Other commonly used surfactants such as Tweens or Spans or other similar emulsifying agents or bioavailability enhancers that are commonly used in manufacturing pharmaceutically acceptable dosage forms can also be used for the purpose of formulation.

For topical administration, the medicament or said pharmaceutical compositions of this invention may be formulated into a variety of dosage forms for topical application. A wide variety of dermatologically acceptable inert excipients well known to the art may be employed. The topical compositions may include liquids, creams, lotions, ointments, gels, sprays, aerosols, skin patches, and the like. Typical inert excipients may be, for example, water, ethyl alcohol, polyvinyl pyrrolidone, propylene glycol, mineral oil, stearyl alcohol and gel-producing substances. All of the above dosages forms and excipients are well known to the pharmaceutical art. The choice of the dosage form is not critical to the efficacy of the composition described herein.

For transmucosal administration, the medicament or said pharmaceutical compositions of this invention may also be formulated in a variety of dosage forms for mucosal application, such as buccal and/or sublingual drug dosage units for drug delivery through oral mucosal membranes. A wide variety of biodegradable polymeric excipients may be used that are pharmaceutically acceptable, provide both a suitable degree of adhesion and the desired drug release profile, and are compatible with the active agents to be administered and any other components that may be present in the buccal and/or sublingual drug dosage units. Generally, the polymeric excipient comprises hydrophilic polymers that adhere to the wet surface of the oral mucosa. Examples of polymeric excipients include, but are not limited to, acrylic acid polymers and copolymers; hydrolyzed polyvinylalcohol; polyethylene oxides; polyacrylates; vinyl polymers and copolymers; polyvinylpyrrolidone; dextran; guar gum; pectins; starches; and cellulosic polymers.

Accordingly, this invention also provides methods of treating mammals, preferably humans, for cancer, which comprises the administration of the medicament or said pharmaceutical composition of this invention that contains a compound of this invention. Such medicament or composition is administered to a mammal, preferably human, by any route that may effectively transports the active ingredient(s) of the composition to the appropriate or desired site of action, such as oral, nasal, pulmonary, transdermal, such as passive or iontophoretic delivery, or parenteral, e.g., rectal, depot, subcutaneous, intravenous, intramuscular, intranasal, ophthalmic solution or an ointment. Further, the administration of the compound of this invention with other active ingredients may be concurrent or simultaneous.

It will be appreciated that the dosage of compounds of the present invention will vary from patient to patient not only for the particular compound or composition selected, the route of administration, and the ability of the compound (alone or in combination with one or more drugs) to elicit a desired response in the patient, but also factors such as disease state or severity of the condition to be alleviated, age, sex, weight of the patient, the state of being of the patient, and the severity of the pathological condition being treated, concurrent medication or special diets then being followed by the patient, and other factors which those skilled in the art will recognize, with the appropriate dosage ultimately being at the discretion of the attendant physician. Dosage regimens may be adjusted to provide the improved therapeutic response. A therapeutically effective amount is also one in which any toxic or detrimental effects of the compound or composition are outweighed by the therapeutically beneficial effects. Preferably, the compounds or compositions of the present invention are administered at a dosage and for a time such that the number and/or severity of the symptoms are decreased.

In the context of this disclosure, a number of terms shall be used.

The term "treating" or "treatment" as used herein refers to administering a compound of this invention to arrest the growth of at least 45%, 50%, 55%, 60% or 65% of the cancerous cells at $G_2$/M cycle, preventing them from multiplying, and hence results in the reduction of the size of the cancer. Therefore, the term "treating" or "treatment" as used herein also refers to kill or induce apoptosis of the cancerous cells.

The term "an effective amount" as used herein refers to an amount effective, at dosages, and for periods of time necessary, to achieve the desired therapeutically desired result with respect to the treatment of cancer.

The terms "compounds", "compositions", "active compounds", "agent" or "medicament" are used interchangeably herein to refer to a compound or compounds or composition of which, when administered to a subject (human or animal) induces a desired pharmacological and/or physiological effect by local and/or systemic action.

The term "administered", "administering" or "administration" are used interchangeably herein to refer means either directly administering a compound or a composition of the present invention, or administering a prodrug, derivative or analog which will form an equivalent amount of the active compound within the body.

The term "subject" or "patient" refers to an animal including the human species that is treatable with the compositions and/or methods of the present invention. The term "subject" or "patient" intended to refer to both the male and female gender unless one gender is specifically indicated. Accordingly, the term "subject" or "patient" comprises any mammal, preferably a human, which may benefit from treatment by the compound of this disclosure.

The present invention will now be described more specifically with reference to the following embodiments, which are provided for the purpose of demonstration rather than limitation.

EXAMPLES

Materials and Methods

Cell and Culture

Cell lines used in the present disclosure include human chronic myelogenous leukemia (CML) cell line K562, Imatinib-resistant K562 cell line K562R, human pancreatic carcinoma, epithelial-like cell line PANC-1, human pancreatic cancer cell line BxPc-3, human large cell lung cancer cell line SEG-1, human esophageal squamous cell carcinoma line 81T/VGH and human esophageal adenocarcinoma line BE-3. Each cell lines were cultured and maintained in Dulbecco's modified Eagle media (DMEM) supplemented with 10% fetal calf serum, 100 IU/ml penicillin, 100 µg/ml streptomycin, and 2 mM glutamine in 5% $CO_2$ at 37° C.

Induction of Drug Resistant CML Cell Line

The CML cell line, K562R, was cultured in the presence of a continuous low dose of imatinib mesylate, which is also termed STI-571, to generate their resistance to imatinib. In operation, K562R cells were maintained in the DMEM supplemented with 10% fetal calf serum (FCS), 100 IU/ml penicillin, 100 µg/ml streptomycin, 2 mM glutamine and 0.2 µM imatinib in 5% $CO_2$ at 37° C.

MTT Assay

MTT assay is a colorimetric assay that measures the activity of enzymes (i.e., reductase) that reduce (3-(4,5-dimethylthiazol-2yl)-2,5-diphenyltetrazoliumbromide (MTT), a yellow tetrazole, to purple formazan, in living cells. This reduction only takes place when cells are alive; hence MTT assay is generally used to assess the viability and proliferation of cells. Briefly, cells were challenged with various doses of the tested compound (e.g., I7457 or I7557) for 48 hours or 72 hours. Then, MTT dye (500 µg/ml) was added and the reaction was allowed to proceed for 4 hours before being terminated by the addition of 500 µl of isopropanol. The absorbance of the solution at 570 nm was measured by spectrophotometer.

Cell Cycle Analysis

Cultured cells with or without pre-treatment of the compounds of this invention (i.e., I7457 or I7557) were harvested from the cultured media and fixed by incubating with 75% iced cold ethanol at 4° C. for at least overnight. The fixed cells were then warmed up to room temperature and treated with RNAase A for about 30 min. Precipitated cells were collected by centrifugation and re-suspended in a buffer solution containing propidium iodine (20 µg/ml) before being subject to flow cytometry analysis, where cell numbers at respective cell cycles were determined.

Immunoblot Analysis

Cultured cells were lysed by use of well known lysing buffer, and total amount of proteins were determined by Bradford method. The extracted raw proteins (about 50-100 µg) were loaded to 0.15% sodium dodecyl sulfate polyacrylamide gel, and proteins therein were separated by electrophoresis. The separated proteins were then transferred to nitrocellulose membrane and non-specific binding was removed by TBST buffer (0.8% NaCl, 0.02% KCl, 25 mM Tris-HCl/pH 8.0 and 0.1% Tween-20) containing 4% skim milk. Antibodies including p-Plk-1, p-Chk-1, p-Chk-2, p-Cdc2, GAPDH, α-tubulin, β-tubulin, and p-histone H3 (purchased from Transduction Laboratories, Lexington, Ky., USA), were respectively dissolved in TBST buffer containing 2% skim milk and incubated with the separated protein bands at 4° C. for at least over night; followed by incubation with horseradish conjugated secondary antibodies at room temperature for about 30 min, and then detected by ECL chemiluminesance detection kit (Amersham Pharmacia Biotech, US).

Liu's Staining

Cells were transferred to a glass coverslide and covered with solution A (0.5 g of methylene blue and 1.7 g of Eosin yellow dissolved in 1,000 ml of ethanol). After 45 seconds, solution B (1.3 g of azure, 1.4 g of methylene blue, 23.38 g of $Na_2HPO_4$, 6.5 g of $KH_2PO_4$, dissolved in 1,000 ml of distilled water) was added in the proportion of 2 parts of B to 1 part of A. Mixed the solutions well by blowing the surface. The slide was left standing for 90 seconds and then washed off the staining solution rapidly by running water. The morphology of stained cells was then examined by observation under microscope.

Radiation Treatment and Clonogenic Assay

Approximately 100 variable tumor cells were respectively plated onto 35-mm six-well culture dishes and were allowed to grow in DMEM medium contained 10% FCS mixed with 5 or 10 μM of the tested drugs (i.e., I7457 or I7557), and the drug-treated cells were continued culture for 24 hours. The drugs were then washed out, and cells were subject to radiation treatment. Specifically, 6 MeV electron beam energy was delivered by a linear accelerator (Clinac 1800, Varian Associates, Inc., Palo Alto, Calif., USA) with a rate of 2.4 Gy/min at various dose including 0, 0.5, 1, 2 and 4 Gy in a single fraction. Full electron equilibrium was ensured for each fraction by a parallel plate PR-60C ionization chamber (CAPINTEL, Inc., Ramsey, N.Y., USA).

After radiation treatment, cells were returned to the culture for another 10 to 14 days; then were stained with 3% crystal violet and the numbers of colony (≥50 cells) were counted.

Example 1

I7457 and I7557 Inhibit the Growth of Drug Resistant CML K562R Cells

The imatinib resistant human chronic myelogenous leukemia (CML) cell line K562R was induced by procedures described above in the "Materials and Methods" Section. Anti-proliferative activity of I7557 and I7557 were respectively assessed by cell viability and cell cycle analysis, as well as by immunoblot and Liu's Staining.

FIGS. 1 and 2 illustrate the effects of I7457 and I7557 on cell viability of imatinib resistant CML cells respectively. It is evident that both I7457 and I7557 are effective in reducing the cell number in a dose dependent manner; and drug resistant CML cell number is reduced to at least 65% of that of the control in the presence of 20 μM of the tested compound.

Cell cycle analysis further indicated that at least 60% of the CML cells are arrested at $G_2$/M phase, with the population of cells in sub-G1 group increases with an increase in the dosage of I7457 or I7557 (see Table 1).

TABLE 1

Effects of I7457 and I7557 On Cell Cycle Of CML Cells

| 24 hours | | Sub-G1% | $G_0/G_1$ | S | $G_2$/M |
|---|---|---|---|---|---|
| Control | | 0.72 ± 0.40 | 36.04 ± 2.94 | 45.41 ± 1.94 | 18.56 ± 4.49 |
| I7457 | 5 μM | 0.79 ± 0.14 | 30.90 ± 0.99 | 47.93 ± 0.80 | 21.17 ± 0.46 |
| | 10 μM | 3.52 ± 0.78 | 29.55 ± 3.17 | 47.98 ± 0.09 | 22.47 ± 3.56 |
| | 20 μM | 2.48 ± 0.29 | 2.87 ± 0.78 | 36.14 ± 2.52 | 60.99 ± 2.78 |
| I7557 | 5 μM | 0.52 ± 0.07 | 30.79 ± 2.28 | 46.38 ± 1.73 | 22.84 ± 0.60 |
| | 10 μM | 1.18 ± 0.08 | 30.52 ± 0.96 | 51.08 ± 0.36 | 18.40 ± 1.16 |
| | 20 μM | 5.33 ± 1.46 | 11.54 ± 6.51 | 23.36 ± 2.45 | 65.10 ± 8.16 |

Further, CML cells started to round up with an appearance of a balloon after being treated with 20 μM of I7457 (FIG. 3B) or I7557 (FIG. 3B), indicating that CML cells were undergoing apotosis and mitotic arrest as compared with that of the control cells (FIG. 3A). The mitotic arrest event was subsequently confirmed by the staining of α- and β-tubulin in the drug-treated CML cells (data not shown), as well as by immunoblot analysis. FIG. 4 depicts the levels of β-tubulin in the drug-treated CML cells measured by immunoblot analysis, in which β-tubulin levels were lowered by the treatment of I7457 and I7557 respectively, as compared with that of the control cells.

I7457 or I7557-induced mitotic arrest process was further investigated by measuring the expressed level of the mitotic inactivation complex proteins such as Cdc2 kinase and cyclin B1; and their upstream regulatory proteins such as Plk-1, Chk-1 and Chk-2. It was found that both the levels of cyclin B1 and phosphorylated Plk-1 increased in I7457 and I7557-treated CML cells respectively (FIGS. 5 and 6); whereas the levels of p-Chk-1, p-Chk-2 and p-cdc2 kinase decreased with treatment of I7457 or I7557 (FIGS. 7, 8, and 9), as compared with that of the control.

The expression of another key mitosis protein, histone H3, was also investigated. Histone H3 is only phosphorylated during mitosis, hence its amount will increase if more cells were arrested in the mitotic phase. As expected, compared with the control cells, the levels of phosphorylated histone H3 were significantly higher in I7457 and I7557-treated drug-resistant CML cells respectively (FIG. 10). The mitosis inhibitor, nocodazole (100 nM), which was known to interfere with microtubule formation of the mitotic cells was employed as a positive control. Taken together, the results above indicate that mitotic events were suppressed in I7457 and I7557-treated drug-resistant CML cells.

Example 2

I7457 and I7557 Inhibit the Growth of Human Pancreatic Carcinoma, Epithelial-Like Cell Line PANC-1

Effects of the compounds of this disclosure, I7457 and I7557 on PANC-1 cells were investigated in accordance with similar procedures described in Example 1, including cell viability assay, cell cycle analysis, immunoblot analysis on the expression of the cell cycle associated proteins, and morphology analysis.

Cell viability assay indicated that both I7457 and I7557, at the concentration of 20 μM, were effective in reducing the cancerous cell number by at least 50%, as compared with that of the control cells (data not shown). Cell cycle analysis revealed that treatment with I7457 and I7557 for merely 24 hours can arrest at lest 50% of the cells at $G_2$/M phase, with the population of cells in sub-G1 group increases with an increase in the dosage of I7457 or I7557 (see Table 2). As to cell cycle associated proteins, their expression pattern were similar to those observed in drug-resistant CML cells (data not shown).

TABLE 2

Effects of I7457 and I7557 On Cell Cycle Of PANC-1 Cells

| 24 hours | | Sub-G1% | $G_0/G_1$ | S | $G_2$/M |
|---|---|---|---|---|---|
| Control | | 1.46 ± 0.07 | 47.77 ± 2.20 | 29.87 ± 2.07 | 22.37 ± 0.78 |
| I7457 | 10 μM | 1.55 ± 0.21 | 45.30 ± 2.67 | 18.46 ± 2.91 | 36.25 ± 0.96 |
| | 20 μM | 2.51 ± 0.58 | 23.93 ± 0.58 | 25.68 ± 2.63 | 5.39 ± 2.17 |
| I7557 | 10 μM | 0.79 ± 0.05 | 45.43 ± 1.27 | 26.19 ± 3.28 | 28.38 ± 2.41 |
| | 20 μM | 2.05 ± 0.44 | 24.71 ± 2.98 | 19.45 ± 3.32 | 55.84 ± 0.63 |

Example 3

I7457 and I7557 Enhance the Susceptibility of Human Pancreatic Cancer Cells to Radiation Treatment In this example, effects of I7457 and I7557 on the susceptibility of human pancreatic cancer cell lines Panc-1 and BxPc-3 to radiation were investigated.

To this purpose, cancerous cells were pre-treated with I7457 or I7557, before being treated with various doses of radiation in accordance with procedures described in "Materials and Methods" section. The survived cells were then subject to clonogenic assay, which is a test generally employed to determine the effect of drugs or radiation on the cells' ability to undergo unlimited division by counting the number of colony formed from a single cell. The colony is defined to consist of at least 50 cells. Results are presented in Tables 3 and 4. Both compounds of this invention, i.e., I7457 and I7557, at dose of 10 μM, are capable of enhancing the susceptibility of PANC-1 and BxPc-3 cells to radiation treatment; hence these compounds of this invention are potential compounds to act as adjuvants for anti-cancer drugs.

TABLE 3

Effects of I7457 and I7557 On Susceptiblity of PANC-1 Cells To Radiation Treatment

| | | Radiation Dosage (Gy) | | | | |
|---|---|---|---|---|---|---|
| | | 0 | 0.5 | 1 | 2 | 4 |
| Control (DMSO) | | 80 | 60 | 66 | 49 | 32 |
| I7457 | 5 μM | 42 | 59 | 48 | 28 | 17 |
| | 10 μM | 33 | 26 | 19 | 14 | 1 |
| I7557 | 5 μM | 60 | 63 | 59 | 48 | 20 |
| | 10 μM | 41 | 26 | 35 | 19 | 6 |

TABLE 4

Effects of I7457 and I7557 On Susceptiblity of BxPC-3 Cells To Radiation Treatment

| | | Radiation Dosage (Gy) | | | | |
|---|---|---|---|---|---|---|
| | | 0 | 0.5 | 1 | 2 | 4 |
| Control (DMSO) | | 33 | 32 | 37 | 35 | 18 |
| I7457 | 5 μM | 37 | 31 | 29 | 21 | 5 |
| | 10 μM | 14 | 4 | 12 | 2 | 1 |
| I7557 | 5 μM | 33 | 37 | 39 | 29 | 9 |
| | 10 μM | 16 | 15 | 8 | 7 | 1 |

Example 4

I7457 and I7557 Inhibit the Growth of Human Non-Small Cell Lung Cancer Cell Line SEG-1

Effects of the compounds of this disclosure, I7457 and I7557 on SEG-1 cells were investigated in accordance with similar procedures described in Example 1, including cell viability assay, cell cycle analysis, immunoblot analysis on the expression of the cell cycle associated proteins, and morphology analysis.

Cell viability assay indicated that both I7457 and I7557, at the concentration of 20 μM, were effective in reducing the cancerous cell number by at least 70%, as compared with that of the control cells (data not shown). Cell cycle analysis revealed that treatment with I7457 for merely 24 hours can arrest at lest 45% of the cells at $G_2/M$ phase, with the population of cells in sub-G1 group increases with an increase in the dosage of I7457 or I7557 (data not shown). As to cell cycle associated proteins, their expression pattern were similar to those observed in drug-resistant CML cells (data not shown).

Example 5

I7457 and I7557 Inhibit the Growth of Human Esophageal Cancer Cell Lines 81T/VGH and BE-3

Effects of the compounds of this disclosure, I7457 and I7557 on the growth of human esophageal squamous cell carcinoma line 81T/VGH and human esophageal adenocarcinoma line BE-3 were investigated in accordance with similar procedures described in Example 1. Results are summarized in Tables 5 and 6, respectively.

For the 81T/VGH cells, cell viability assay indicated that after treatment for 48 hours, both I7457 and I7557, at the concentration of 20 μM, were effective in reducing the cancerous cell number by at least 50%; as compared with that of the control cells (see Table 5). Similar results were also found for BE-3 cells, about 50% of cancerous cells' growth inhibition were found for both I7457 and I7557 at a concentration of 20 μM (see Table 6).

TABLE 5

Effects of I7457 and I7557 On Cell Viability of 81T/VGH Cells

| | | 48 hours after Drug Treatment | | | | |
|---|---|---|---|---|---|---|
| | | I | II | III | Average | % of inhibition |
| Control (DMSO) | | 2.140 | 2.512 | 1.937 | 2.196 ± 0.168 | 0 |
| I7457 | 10 μM | 0.936 | 1.346 | 1.261 | 1.181 ± 0.125 | 45.871 ± 6.165 |
| | 20 μM | 0.465 | 0.644 | 0.739 | 0.616 ± 0.081 | 71.502 ± 4.957 |
| I7557 | 10 μM | 1.324 | 1.682 | 1.537 | 1.514 ± 0.104 | 30.599 ± 5.181 |
| | 20 μM | 0.804 | 0.991 | 1.100 | 0.965 ± 0.086 | 55.402 ± 6.105 |

TABLE 6

Effects of I7457 and I7557 On Cell Viability of BE-3 Cells

| | | 48 hours after Drug Treatment | | | | |
|---|---|---|---|---|---|---|
| | | I | II | III | Average | % of inhibition |
| Control (DMSO) | | 2.178 | 2.140 | 2.379 | 2.232 ± 0.074 | 0 |
| I7457 | 10 μM | 1.321 | 1.400 | 1.538 | 1.420 ± 0.063 | 36.413 ± 1.476 |
| | 20 μM | 1.035 | 1.085 | 1.200 | 1.107 ± 0.049 | 50.443 ± 1.017 |
| I7557 | 10 μM | 1.581 | 1.534 | 1789 | 1.635 ± 0.078 | 26.823 ± 1.047 |
| | 20 μM | 1.105 | 1.147 | 1.201 | 1.151 ± 0.028 | 48.402 ± 1.005 |

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of treating cancer in a subject comprising administering to the subject an effective amount of 6-methylsulfonylhexyl isothiocyanate or a pharmaceutically acceptable salt thereof, wherein the cancer is selected from the group consisting of pancreatic cancer, imatinib resistant chronic myelogenous leukemia (CML), non-small-cell carcinoma, and esophageal cancer.

2. The method of claim 1, wherein the subject is a human.

* * * * *